United States Patent [19]
Colleran et al.

[11] Patent Number: 5,944,723
[45] Date of Patent: Aug. 31, 1999

[54] LOCKING ORTHOPAEDIC CLAMPING TOOL

[75] Inventors: Dennis P. Colleran, Plainville; Justin Dye, Mansfield; Brian Duffy, Taunton, all of Mass.

[73] Assignee: Johnson & Johnson Professional, Inc., Raynham, Mass.

[21] Appl. No.: 09/049,535

[22] Filed: Mar. 27, 1998

[51] Int. Cl.[6] .................................................. A61B 17/56
[52] U.S. Cl. ............................................ 606/88; 606/208
[58] Field of Search .................................. 606/88, 87, 86, 606/72, 205, 206, 207, 208; 81/300, 318, 324, 341, 381, 427.5

[56] References Cited

U.S. PATENT DOCUMENTS

| | | |
|---|---|---|
| 2,574,676 | 11/1951 | Waterbury . |
| 4,499,797 | 2/1985 | Wilson ........................................ 81/367 |
| 4,706,660 | 11/1987 | Petersen .............................. 128/92 VW |
| 5,050,464 | 9/1991 | Hurtig ........................................ 81/90.1 |
| 5,129,907 | 7/1992 | Heldreth et al. ........................... 606/80 |
| 5,284,482 | 2/1994 | Mikhail ...................................... 606/86 |
| 5,531,750 | 7/1996 | Even-Esh ................................... 606/79 |
| 5,536,271 | 7/1996 | Daly et al. ................................. 606/80 |
| 5,575,793 | 11/1996 | Carls et al. ................................ 606/80 |
| 5,658,291 | 8/1997 | Techiera ..................................... 606/80 |
| 5,702,408 | 12/1997 | Wales et al. ............................. 606/139 |

OTHER PUBLICATIONS

"Surgical Technique For use with PFC® Modular Total Knee System", Universal Inset Patella, consisting of three pages including cover page unnumbered, page 10 and page 12.

Product Display Craftsman Professional Auto Lock, "Automatic Self–Sizing Locking Pliers 7 Straight Jaw", made in the USA.

Primary Examiner—Guy V. Tucker
Attorney, Agent, or Firm—Nutter, McClennen & Fish, LLP

[57] ABSTRACT

A self-locking orthopaedic clamp includes first and second jaws, each jaw having a work engaging surface and a handle comprising first and second actuation members, each actuation member having a first end proximate to the first and second jaws and a second opposed end, and the second actuation member being rigidly coupled to and integral with the second jaw. A four-bar linkage connects the first and second jaws and the first and second actuation members. The design of the clamp and the four-bar linkage is such that the clamp is self-locking. The clamp may be configured for use in a variety of orthopaedic procedures, but it is especially useful for clamping a prosthesis to a resected natural patella.

33 Claims, 4 Drawing Sheets

5,944,723

LOCKING ORTHOPAEDIC CLAMPING TOOL

CROSS-REFERENCE TO RELATED APPLICATION

Not Applicable.

STATEMENT REGARDING FEDERALLY SPONSORED RESEARCH

Not Applicable.

FIELD OF THE INVENTION

The present invention relates to an orthopaedic clamping tool having a four bar linkage.

BACKGROUND OF THE INVENTION

In a variety of orthopaedic procedures, the surgeon must use a clamp to hold a bone in a stationary position. Often, the clamping is required so that the surgeon may steady the bone so that he may perform some cutting or other procedure on the bone, or the surgeon may clamp a cemented object to a bone so that the object remains stationary while the cement cures and the object permanently attaches to the bone. One such orthopaedic procedure requiring the use of an orthopaedic clamp is the implantation of a patellar prosthesis.

The patella, commonly known as the kneecap, is a hard bone having an articular surface of cartilage on the posterior side. The articular surface is held in place against the femoral condyles by the patella tendon where it provides leverage that is necessary to a properly functioning knee joint. If the articular surface becomes damaged by trauma or by degeneration, proper knee functioning breaks down, often accompanied by joint pain and immobility. In such situations, a patella prosthesis, sometimes referred to as a button, may be inserted to restore normal functioning to the knee.

Patella prostheses have also been used in total knee replacement surgery to insure a reproducible interaction of a patella with the femoral and tibial portions of the total knee replacement. Usually in such procedures the posterior side of the patella is prepared, sized and reamed so that a patella implant, when fixed to the patella, restores the reconstructed patella to its natural or original thickness.

In one procedure, the patella is prepared for the patellar implant as follows. A patellar holding clamp is placed on the patella with a clamp ring on the posterior side. The patella is then reamed with a patella reamer to a predetermined depth. One method of determining when the reamer has reached the appropriate depth involves placing a guide member on the patellar holding clamp and a stop member on the reamer. The reamer is then urged toward the patella, guided by the guide member and the clamp ring until the stop member abuts the guide member. Clamps useful for this purpose are disclosed, for example, in U.S. Pat. Nos. 5,129,907; 5,284,482; and 5,575,793.

The patellar implant is then inserted, often with a bone cement, into the prepared bed. A patellar holding clamp may be used to push the patellar implant into the prepared bed, or to hold the implant in place while the bone cement cures. Clamps useful for this purpose are shown in U.S. Pat. No. 4,706,660 (clamp 110) and in Johnson & Johnson Orthopaedics Universal Inset Patella Surgical Technique For use with PFC® Modular Total Knee System.

The prior art clamps are generally useful for their intended purposes, but each requires the use of two hands to set and lock the clamp in place as is necessary to perform cutting or setting operations on the target bone. Accordingly, it would be advantageous to provide a clamping tool that can be operated with one hand and that automatically locks onto the bone being clamped with a predetermined clamping force.

SUMMARY OF THE INVENTION

The present invention provides a self-locking orthopaedic clamp. The self-locking orthopaedic clamp includes first and second jaws, each jaw having a work engaging surface, and a handle comprising first and second actuation members, each actuation member having a first end proximate to the first and second jaws and a second opposed end.

A four-bar linkage connects the first and second jaws and the first and second actuation members. The four-bar linkage includes a first link integral with the first jaw and rotatably coupled to the second jaw at a first pivot point and to the first actuation member proximate to the first end thereof at a second pivot point; a second link integral with the first actuation member and rotatably coupled to the first link at the second pivot point; a third link rotatably coupled to the first actuation member at a third pivot point located on the first actuation member toward the second end thereof from the second pivot point and rotatably and slidably coupled to the second actuation member at a fourth, sliding pivot point; and a fourth link integral with the second jaw and the second actuation member and rotatably coupled to the first link at the first pivot point and rotatably and slidably coupled to the third link at the fourth, sliding pivot point.

The sliding of the fourth pivot point locks so as to provide a predetermined clamping force at the work engaging surfaces of the first and second jaws within a predetermined clamping distance range between the work engaging surfaces.

The locking of the fourth pivot point may be effected by providing a sliding member and a locking member within a hollow second actuation member. The sliding member has a rotatable connection with the third link, and a sliding surface that slides on one of two opposed inner surfaces of the hollow second actuation member in order to provide the rotatable and slidable coupling between the third and fourth links. The locking member also has a sliding surface and slides on the other of the opposed inner surfaces of the hollow second actuation member. The sliding and locking members are provided with opposed complementary wedge surfaces that are arranged so that, as the locking member moves toward the second end of the second actuation member with respect to the locking member, the wedge surfaces engage to push the locking and sliding members toward the opposed inner surfaces of the hollow second actuation member, causing an increase in friction at the sliding surfaces that locks the sliding and locking members in place.

The relative motion that locks the sliding and locking members in place may be provided by configuring a contact region on the third link that pushes the locking member toward the second end of the second actuation member as the fourth sliding pivot point slides in that same direction during closure of the handle. The contact region is configured to disengage from the locking member before the sliding member reaches the end of its range of motion. Accordingly, the sliding member will be forced toward the second end of the second actuation member with respect to the locking member after the contact region on the third link has disengaged from the locking member.

An adjustable contact member may also be provided on the locking member. Using the adjustable contact member, a surgeon may adjust the orthopaedic clamp of the invention to apply a predetermined clamping force within a predetermined clamping range.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
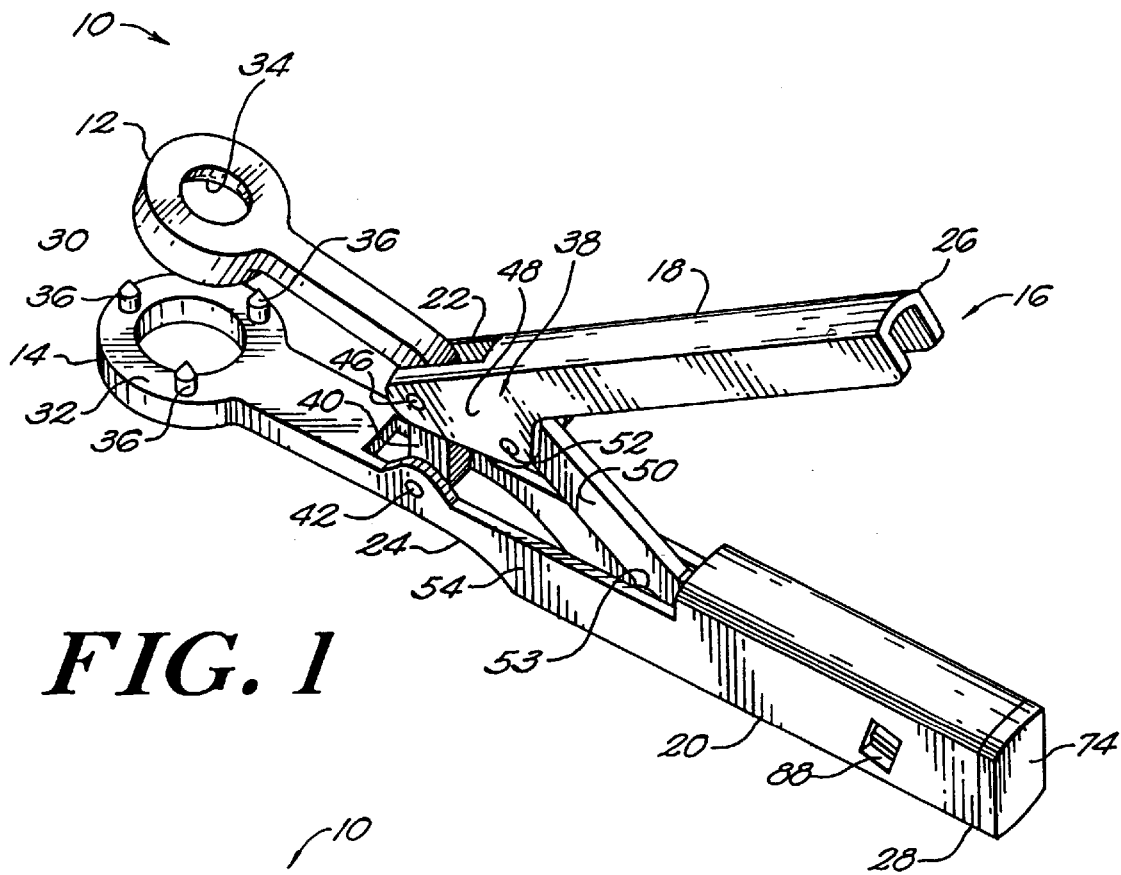
FIG. 1 is a perspective view of a locking orthopaedic clamp of the invention shown in an open, unlocked position.
Figure 2:
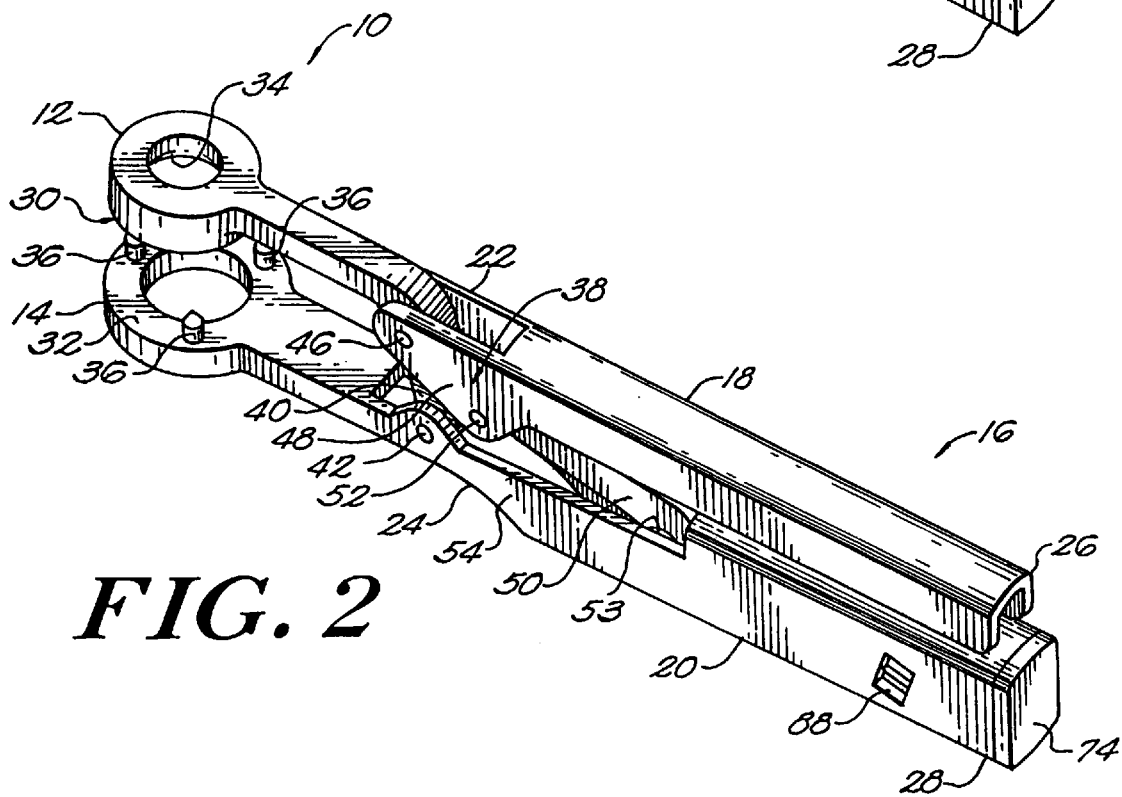
FIG. 2 is a perspective view of the locking orthopaedic clamp of FIG. 1 in a closed, locked position.
Figure 3:
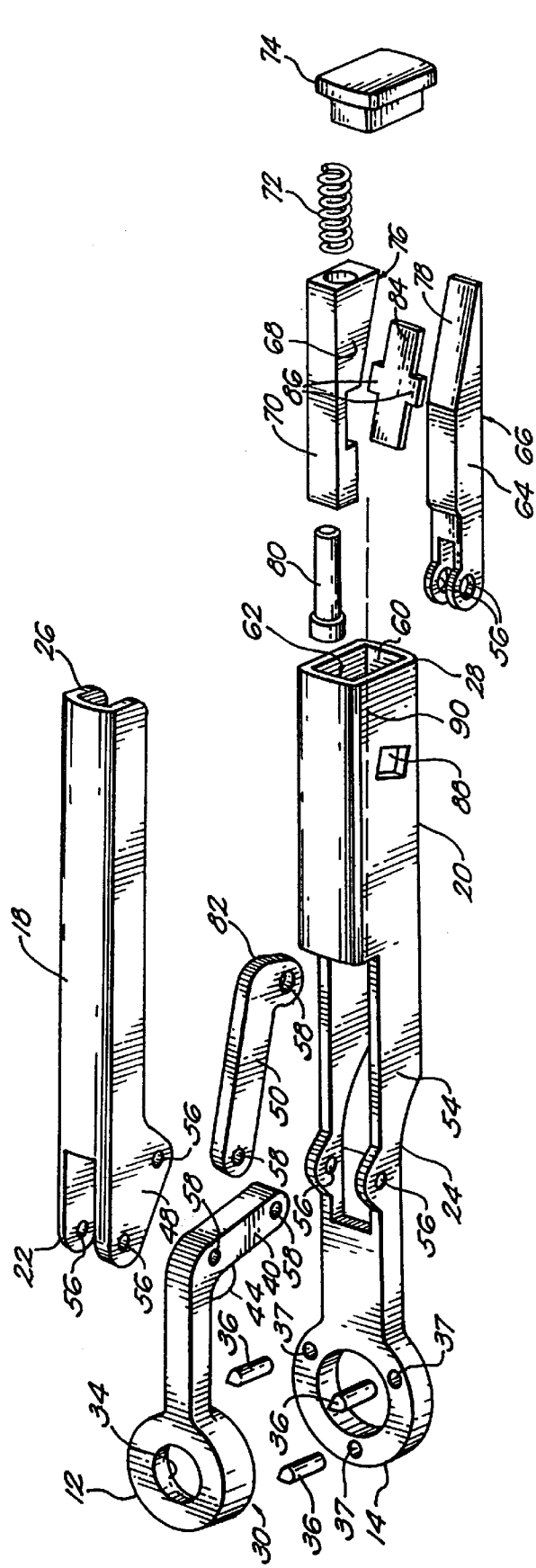
FIG. 3 is an exploded view of the clamp of FIG. 1.

A locking orthopaedic clamp 10 of the invention, illustrated in FIGS. 1 to 3, includes first and second jaws 12, 14 and a handle portion 16 having first and second actuation members 18, 20. Each actuation member 18, 20 has a first end 22, 24 proximate to the first and second jaws 12, 14 and a second opposed end 26, 28. The second actuation member 20 is rigidly coupled to and integral with the second jaw 14.

The jaws 12, 14 are circular and have opposed work engaging surfaces 30, 32. The work engaging surface 30 of first jaw 12 has an annular engagement surface 34 suitable for contacting a patellar prosthesis. The work engaging surface 32 of second jaw 14 includes three elongate pins 36 which are seated in corresponding recesses 37 in the second jaw 14. Pins 36 are useful for engaging and centering a patella within the orthopaedic clamp 10 and may or may not penetrate the surface of a patella engaged between the jaws 12, 14. Of course, work engaging surfaces 30, 32 could be configured by a person of ordinary skill in the art for other orthopaedic uses.

A four-bar linkage 38 connects the first and second jaws 12, 14 with the first and second actuation members 18, 20. The four-bar linkage 38 includes a first link 40 integral with the first jaw 12 and rotatably coupled to the second jaw 14 at a first pivot point 42. First jaw 12 forms an angle 44 with first link 40 so that, as the jaws 12, 14 are moved toward each other to engage a workpiece, the jaws 12, 14 will be substantially parallel when the workpiece is engaged. First link 40 is also rotatably coupled to the first actuation member 18 proximate to the first end 22 thereof at a second pivot point 46.

A second link 48 is integral with the first actuation member 18 and rotatably coupled to the first link 40 at the second pivot point 46. A third link 50 is rotatably coupled to the first actuation member 18 at a third pivot point 52 located on the first actuation member 18 toward the second end 26 thereof from the second pivot point 46. The third link 50 is also rotatably and slidably coupled to the second actuation member 20 at a fourth, sliding pivot point 53.

A fourth link 54 is integral with the second jaw 14 and the second actuation member 20. The fourth link 54 is rotatably coupled to the first link 40 at the first pivot point 42 and rotatably and slidably coupled to the third link 50 at the fourth sliding pivot point 53.

As shown in FIG. 1, wherein an orthopaedic clamp 10 of the invention is shown in an open, unlocked position, the second and fourth links 48, 54 are integral with the first and second actuation members 18, 20, respectively, and are generally parallel to each other (in the position shown), and mark a top and bottom of the four bar linkage 38. The first link 40 is rotatably connected to each of the second and fourth links 48, 54 proximate to the first end 22, 24 (the left side as shown) of the actuation members 18, 20. The third link 50 is rotatably connected to the fourth link 54 in a location that is toward the second end 26, 28 (the right side as shown) of the actuation members 18, 20 with respect to the first link 40 connections.

The rotatable connections may be formed at each of the pivot points 42, 46, 52, 53 using substantially cylindrical pivot pins (not shown) to rotatably connect the links. The second and fourth links 48, 54, which are integral with the actuation members 18, 20, provide two separated through holes 56 (FIG. 3) for each rotatable connection while the first and third links 40, 50 each have a single through hole 58 for each rotatable connection. The links are connected by sliding the appropriate through hole 58 of the first or third link 40, 50 between the corresponding two through holes 58 of the second or fourth link 48, 54 until the holes are linearly arranged. A pivot pin extends through the linearly arranged holes to rotatably connect the links. A person of ordinary skill in the art will understand that other methods of rotatably connecting the links may be employed without departing from the spirit of the invention.

The second actuation member 20 may have a tubular form, being hollow with first and second opposed inner surfaces 60, 62 (FIG. 3). A sliding member 64 has a sliding surface 66 that is slidingly engaged with the first inner surface 60 of the second actuation member 20. The sliding member 64 has two separated through holes 58 arranged to rotatably couple with the third link 50 at the fourth, sliding pivot point 53. In order for the orthopaedic clamp 10 of the invention to perform with the required level of precision for surgical use, the sliding surface 66 and the first inner surface 60 of the second actuation member 20 are preferably formed from a metal, such as stainless steel, having a hardness of at least about 40 on the Rockwell C scale and having a surface roughness of no more than about 125 microns on their slidingly engaged surfaces.

A locking member 68 is also provided within the hollow second actuation member 20 having a sliding surface 70 that is slidingly engaged with the second inner surface 62 of the second actuation member 20. The locking member sliding surface 70 and the first inner surface 62 of the second actuation member 20 are preferably formed from a metal, such as stainless steel, having a hardness of at least about 40 on the Rockwell C scale and have a surface roughness of no more than about 125 microns on their slidingly engaged surfaces. The locking member 70 may be biased, such as by spring 72 placed between the locking member 68 and an end cap 74 fixable at the second end 28 of the second actuation member 20, toward the first end 24 of the second actuation member 20.

Locking member 68 has a wedge surface 76 opposed to its sliding surface 70 that corresponds to a complementary wedge surface 78 on the sliding member 64. The complementary wedge surfaces 76, 78 are arranged so that when the sliding member 64 slides towards the second end 28 of the second actuation member 20 with respect to the locking member 68, the wedge surfaces 76, 78 engage so as to force the sliding member 64 and the locking member 68 away from each other and towards the opposed inner surfaces 60, 62 of the hollow second actuation member 20. These forces cause an increase in friction between the sliding surfaces 66, 70 and the inner surfaces 60, 62 of the hollow second actuation member 20 that locks the sliding member 64 and the locking member 68 against sliding within the second actuation member 20.

The locking member 68 also has an adjustable contact member 80 disposed on the locking member 68 facing in a direction toward the first end 24 of the second actuation member 20. This adjustable contact member 80 may be an adjustable set screw having a knurled knob. Preferably, the locking member 68 is provided wholly within the hollow second actuation member 20, while leaving the adjustable contact member 80 accessible for a surgeon to adjust, at least while the clamping tool 10 is in an open position. The adjustable contact member 80 makes contact with a contact region 82 provided on the third link 50.

A friction member 84 may be provided between the complementary wedge surfaces 76, 78. As shown in FIG. 3, friction member 84 may be elongate with transverse tabs 86 which engage opposed holes 88 (one shown) in the second actuation member 20 to prevent the friction member 84 from sliding in a direction along a longitudinal axis 90 of the second actuation member 20.

Figure 4:
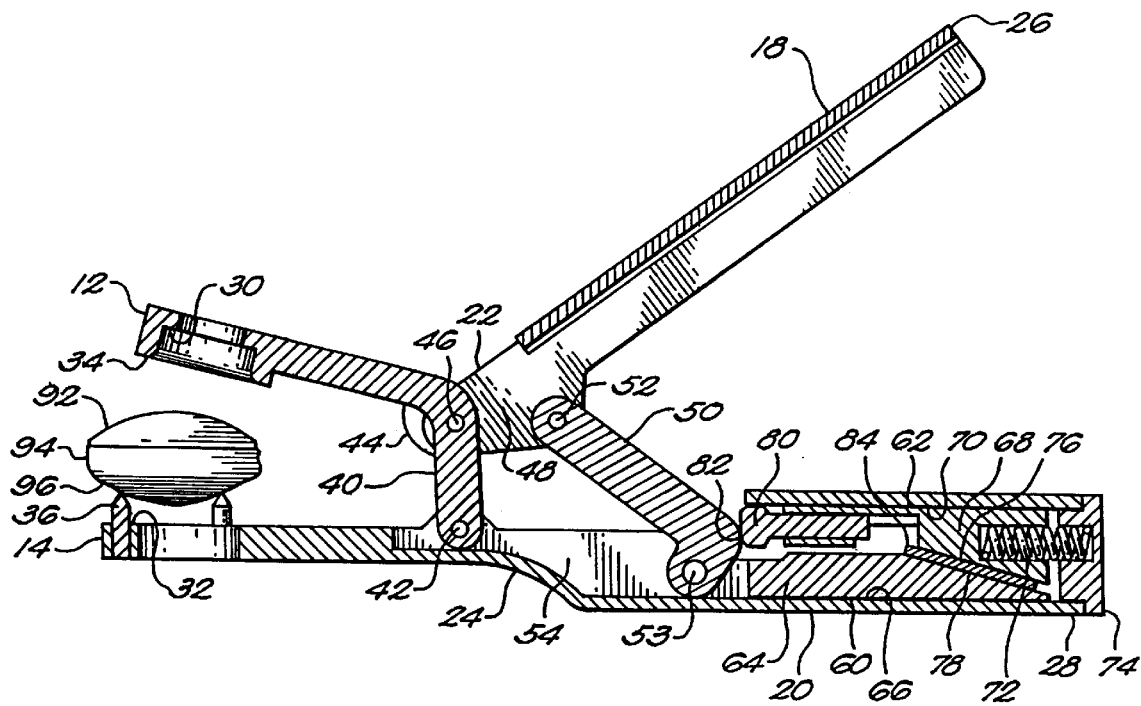
FIG. 4 is a cross sectional view of the clamp of FIG. 1 holding a patella in an open, unlocked position.
Figure 5:
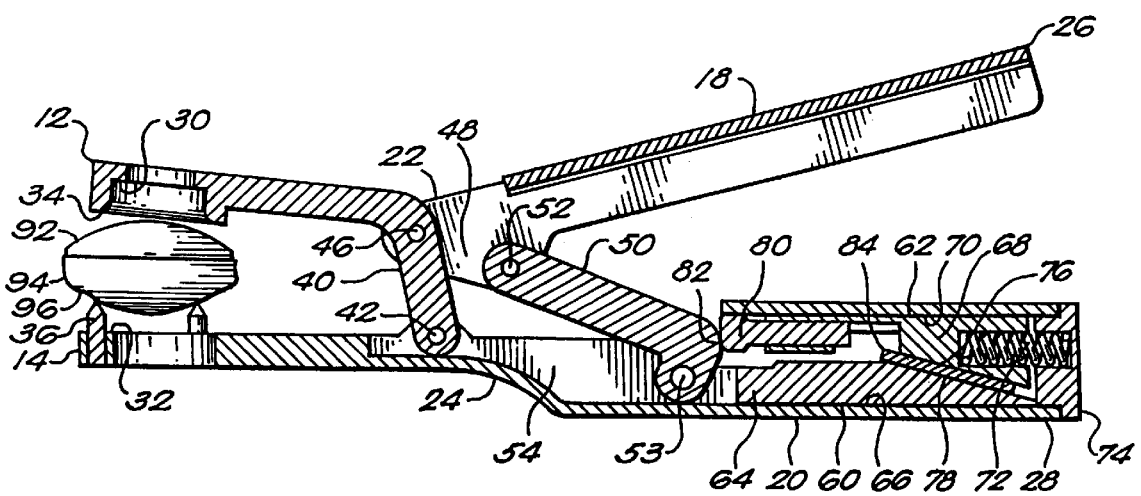
FIG. 5 is a cross sectional view of the patella and clamp of FIG. 4 in a partially closed, unlocked locked position.

Use of the orthopaedic clamp 10 of the invention to hold a patellar prosthesis 92 to a patella 94, illustrated in FIGS. 4–7, begins by contacting the anterior portion 96 of a patella 94 with the work engaging surface 32 of the second jaw 14 while the orthopaedic clamp 10 is in an open, unlocked position as shown in FIG. 4. Next, as the actuation members 18, 20 are moved toward each other, the work engaging surface 30 of the first jaw 12 approaches the patellar prosthesis 92 on the patella 94 (FIG. 5). The actuation members 18, 20 are preferably configured so that a surgeon may grasp both actuation members 18, 20 with one hand in order to bring them together.

Also, the jaws are configured so that as the first jaw 12 approaches the patellar prosthesis 92, the first jaw 12 becomes substantially parallel with the second jaw 14. Preferably, the first and second jaws 12, 14 are substantially parallel to each other within a predetermined clamping range. Generally, for a patella clamping tool, this predetermined clamping range will be between about 8 and 40 millimeters. More preferably, the predetermined clamping range for a patella clamping tool will be between about 25 and 30 millimeters.

Continued squeezing together of the actuation members 18, 20 will cause the work engaging surface 30 of the first jaw 12 to contact the patellar prosthesis 92 while the clamping tool 10 is still in an unlocked condition. Further squeezing after the work engaging surface 30 of the first jaw 12 has contacted the patellar prosthesis xx causes the third link 50 to push the sliding member 64 in a direction toward the second end 28 of the second actuation member 20 along the longitudinal axis 90. Simultaneously, the contact region 82 of the third link 50 presses against the adjustable contact member 80 on the locking element 68, forcing the locking element 68 to slide toward the second end 28 of the second actuation member 20 as well.

Figure 6:
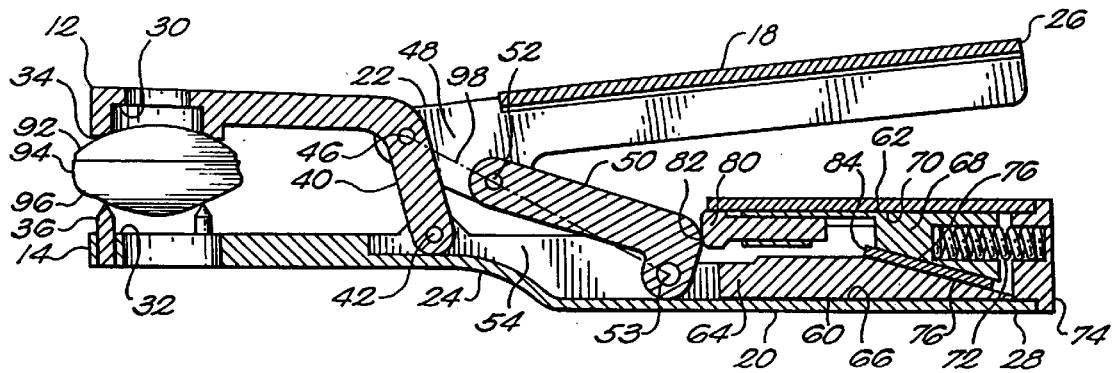
FIG. 6 is a cross sectional view of the patella and clamp of FIG. 4 in a partially closed, unlocked locked position.
Figure 7:
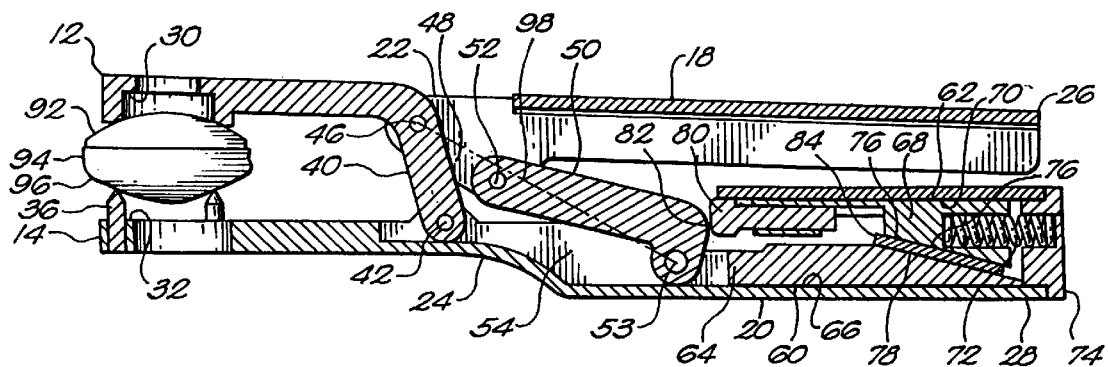
FIG. 7 is a cross sectional view of the patella and clamp of FIG. 4 in a closed, locked position.

During squeezing of the actuation members 18, 20 together by a surgeon, the third pivot point 52 approaches a position along a line 98 defined by the second and fourth pivot points 46, 53 (FIG. 6). Before the third pivot point 52 approaches this line 98, the contact region 82 on the third link 50 disengages from the adjustable contact element 80 and stops forcing the locking element 68 toward the second end 28 of the second actuation member 20. While the disengagement occurs before the third pivot point 52 reaches line 98, the exact timing of the disengagement is determined by the configuration of the third link 50 and the contact area 82 and by the position of the adjustable contact member 80. For the operating ranges disclosed herein, the relative motion and relative timing of the movement between the sliding and locking members 64, 68 may be very slight.

As the third link 50 stops forcing the locking element 68 toward the second end 28 of the second actuation member 20, the third link 50 continues to force the sliding member 64 in that direction until the third pivot point 52 reaches the line 98. As a result of the force applied to the sliding member 64 after the force has been disengaged from the locking member 68, the wedge surface 78 of the sliding member 64 is forced into the wedge surface 76 of the locking member 68, forcing the sliding surfaces 66, 70 of the sliding member 64 and locking member 68 into the opposed inner surfaces 60, 62 of the second actuation member 20 and causing a friction lock that prevents the fourth sliding pivot point 53 from sliding.

Further continued squeezing of the actuation members 18, 20 causes the third pivot point 52 to pass through the line 98 defined by the second and fourth pivot points 46, 53 (FIG. 7) and the orthopaedic clamp 10 locks in a closed position. The orthopaedic clamp 10 can be unlocked and opened again simply by pulling the actuation members 18, 20 apart.

The force applied on the patella 94 at the jaws 12, 14 depends upon the position of the adjustable contact member 80 and may be set to predetermined levels. If the adjustable contact member 80 is moved toward the second end 28 of the second actuation member 18, the force applied at the jaws 12, 14 increases. If the adjustable contact member 80 is provided as a set screw with right-handed threads, this movement may be effected by rotating the set screw in a clock-wise direction. If the adjustable contact member 80 is moved toward the first end 24 of the second actuation member 20, the force applied at the jaws 12, 14 decreases. Generally, for orthopaedic applications, the force applied at the jaws 12, 14 will preferably be between about 5 and 60 pounds, more preferably between about 15 and 40 pounds, within a predetermined clamping range.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A self-locking orthopaedic clamping tool comprising:
    first and second jaws, each jaw having a work engaging surface;
    a handle comprising first and second actuation members, each actuation member having a first end proximate to the first and second jaws and a second opposed end, and the second actuation member being rigidly coupled to and integral with the second jaw;
    a four-bar linkage connecting the first and second jaws and the first and second actuation members and comprising:
        a first link integral with the first jaw and rotatably coupled to the second jaw at a first pivot point and to the first actuation member proximate to the first end thereof at a second pivot point;

a second link integral with the first actuation member and rotatably coupled to the first link at the second pivot point;

a third link rotatably coupled to the first actuation member at a third pivot point located on the first actuation member toward the second end thereof from the second pivot point and rotatably and slidably coupled to the second actuation member at a fourth, sliding pivot point located on a sliding member that is slidably engaged with the second actuation member; and a fourth link integral with the second jaw and the second actuation member and rotatable coupled to the first link at the first pivot point and rotatably and slidably coupled to the third link at the fourth, sliding pivot point; and a locking member located on the second actuation member and capable of a locking engagement with the sliding member to stop the sliding thereof, wherein the sliding of the fourth pivot point locks so as to provide a predetermined clamping force at the work engaging surfaces of the first and second jaws within a predetermined clamping distance range between the work engaging surfaces, and wherein the second actuation member is hollow and has first and second opposed inner surfaces, the sliding member is slidingly engaged with the first inner surface and has a wedge surface, the locking member is located on the second inner surface and has a complementary wedge surface which engages the wedge surface on the sliding member to prevent the sliding thereof.

2. The clamp of claim 1, wherein the locking member is slidingly engaged with the second inner surface.

3. The clamp of claim 2, wherein the locking member slides toward the second end of the second actuation member in response to physical contact with the third link.

4. The clamp of claim 3, wherein an adjustable contact member is provided on the locking member for contact with the third link.

5. The clamp of claim 4, wherein the adjustable contact member is a set screw.

6. The clamp of claim 3, wherein a bias means urges the locking member toward the first end of the second actuation member.

7. The claim of claim 6, wherein the bias means is a compression spring located proximate to the second end of the second actuation member.

8. The clamp of claim 3, wherein the third link is configured so that, as the actuation members are moved toward each other, the third link disengages from the locking member before the third pivot point passes through a line defined by the second and fourth pivot points.

9. The clamp of claim 8, wherein, as a result of continued movement of the actuation members toward each other after the third link has disengaged from the locking member, the sliding member continues to slide toward the second end of the second actuation member, thereby engaging the complementary wedge surfaces of the sliding member and the locking member to lock the sliding member in place.

10. The clamp of claim 1, wherein the predetermined clamping range is about 8 to 40 mm.

11. The clamp of claim 1, wherein the predetermined clamping range is about 25 to 30 mm.

12. The clamp of claim 1, wherein the predetermined clamping force is between about 5 and 60 pounds.

13. The clamp of claim 1, wherein the work engaging surfaces are configured to engage a patella.

14. The clamp of claim 13, wherein a least one jaw has an opening sufficient to allow a patellar reamer to pass through the jaw to engage a surface of the patella.

15. The clamp of claim 1, wherein the work engaging surface of one jaw is configured to engage a patella and the other work engaging surface of the other jaw is configured to engage a patellar prosthesis.

16. The clamp of claim 1, further comprising a friction member located between the complementary wedge surfaces of the sliding and locking members.

17. The clamp of claim 16, wherein the friction member is physically restrained against motion in the direction of the second end of the second actuation member.

18. The clamp of claim 1, wherein when the first and second actuation members are moved toward each other, the third pivot point passes across a line defined by the second and fourth pivot points and thereby locks the first and second jaws in a closed position.

19. A self-locking patellar clamping tool comprising:

first and second jaws, each jaw having a work engaging surface;

a handle comprising first and second actuation members, each actuation member having a first end proximate to the first and second jaws and a second opposed end, the second actuation member being rigidly coupled to and integral with the second jaw, the second actuation member being hollow and having first and second opposed inner surfaces;

a four-bar linkage connecting the first and second jaws and the first and second actuation members and comprising:

a first link integral with the first jaw and rotatably coupled to the second jaw at a first pivot point and to the first actuation member proximate to the first end thereof at a second pivot point;

a second link integral with the first actuation member and rotatably coupled to the first link at the second pivot point;

a third link rotatably coupled to the first actuation member at a third pivot point located on the first actuation member toward the second end thereof from the second pivot point and rotatably and slidably coupled to the second actuation member at a fourth, sliding pivot point; and a fourth link integral with the second jaw and the second actuation member and rotatably coupled to the first link at the first pivot point, rotatably and slidably coupled to the third link at the fourth, sliding pivot point, and located on a sliding member that is slidably engaged with the first inner surface of the second actuation member; and a locking member located on the second inner surface and having a complementary wedge surface which engages the wedge surface on the sliding member to prevent the sliding thereof, wherein when the first and second actuation members are moved toward each other, the third pivot point passes across a line defined by the second and fourth pivot points and thereby locks the first and second jaws in a closed position, and wherein the sliding of the fourth pivot point locks so as to provide a predetermined clamping force at the work engaging surfaces of the first and second jaws within a predetermined clamping distance range between the work engaging surfaces.

20. The clamp of claim 21, wherein the locking member is slidingly engaged with the second inner surface.

21. The clamp of claim 20, wherein the locking member slides toward the second end of the second actuation member in response to physical contact with the third link.

22. The clamp of claim 21, wherein an adjustable contact member is provided on the locking member for contact with the third link.

23. The clamp of claim 22, wherein the adjustable contact member is a set screw.

24. The clamp of claim 21, wherein a bias means urges the locking member toward the first end of the second actuation member.

25. The claim of claim 24, wherein the bias means is a compression spring located proximate to the second end of the second actuation member.

26. The clamp of claim 21, wherein the third link is configured so that, as the actuation members are moved toward each other, the third link disengages from the locking member before the third pivot point passes through a line defined by the second and fourth pivot points.

27. The clamp of claim 26, wherein, as a result of continued movement of the actuation members toward each other after the third link has disengaged from the locking member, the sliding member continues to slide toward the second end of the second actuation member, thereby engaging the complimentary wedge surfaces of the sliding member and the locking member to lock the sliding member in place.

28. The clamp of claim 19, wherein the predetermined clamping range is about 8 to 40 mm.

29. The clamp of claim 19, wherein the predetermined clamping range is about 25 to 30 mm.

30. The clamp of claim 19, wherein the predetermined clamping force is between about 5 and 60 pounds.

31. The clamp of claim 19, wherein the work engaging surfaces are configured to engage a patella.

32. The clamp of claim 31, wherein a least one jaw has an opening sufficient to allow a patellar reamer to pass through the jaw to engage a surface of the patella.

33. The clamp of claim 32, wherein the work engaging surface of one jaw is configured to engage a patella and the other work engaging surface of the other jaw is configured to engage a patellar prosthesis.

* * * * *